(12) United States Patent
Henderson et al.

(10) Patent No.: US 7,344,832 B2
(45) Date of Patent: Mar. 18, 2008

(54) METHOD AND APPARATUS FOR MOLECULAR ANALYSIS IN SMALL SAMPLE VOLUMES

(75) Inventors: Eric Henderson, Ames, IA (US); Curtis Mosher, Ames, IA (US); Janice Huff, Ames, IA (US)

(73) Assignee: BioForce Nanosciences, Inc., Ames, IA (US)

( * ) Notice: Subject to any disclaimer, the term of this patent is extended or adjusted under 35 U.S.C. 154(b) by 56 days.

(21) Appl. No.: 10/541,013

(22) PCT Filed: Dec. 30, 2003

(86) PCT No.: PCT/US03/41770

§ 371 (c)(1),
(2), (4) Date: Jun. 28, 2005

(87) PCT Pub. No.: WO2004/060044

PCT Pub. Date: Jul. 22, 2004

(65) Prior Publication Data

US 2006/0035234 A1  Feb. 16, 2006

Related U.S. Application Data

(60) Provisional application No. 60/437,674, filed on Jan. 2, 2003.

(51) Int. Cl.
*C12Q 1/68* (2006.01)
(52) U.S. Cl. .......................................................... 435/6
(58) Field of Classification Search .................... 435/6, 435/4, 7.1, 7.92, 283.1, 287.1, 287.2; 436/518; 422/50, 58
See application file for complete search history.

(56) References Cited

U.S. PATENT DOCUMENTS

| | | | |
|---|---|---|---|
| 4,728,591 A | 3/1988 | Clark et al. |
| 5,106,729 A | 4/1992 | Lindsay et al. |
| 5,138,174 A | 8/1992 | Tang |
| 5,143,854 A | 9/1992 | Pirrung et al. |
| 5,150,392 A | 9/1992 | Hohn et al. |
| 5,304,487 A | 4/1994 | Wilding et al. |
| 5,314,829 A | 5/1994 | Coles |
| 5,346,683 A | 9/1994 | Green et al. |
| 5,363,697 A | 11/1994 | Nakagawa |
| 5,372,930 A | 12/1994 | Colton et al. |
| 5,384,261 A | 1/1995 | Winkler et al. |
| 5,440,122 A | 8/1995 | Yasutake |
| 5,443,791 A | 8/1995 | Cathcart et al. |
| 5,445,934 A | 8/1995 | Fodor et al. |
| 5,445,971 A | 8/1995 | Rohr |
| 5,453,970 A | 9/1995 | Rust et al. |
| 5,467,642 A | 11/1995 | Hosaka et al. |
| 5,472,881 A | 12/1995 | Beebe et al. |
| 5,482,601 A | 1/1996 | Ohshima et al. |
| 5,514,540 A | 5/1996 | Teoule et al. |
| 5,514,550 A | 5/1996 | Findlay et al. |
| 5,519,212 A | 5/1996 | Elings et al. |
| 5,532,128 A | 7/1996 | Eggers et al. |
| 5,571,639 A | 11/1996 | Hubbell et al. |
| 5,601,982 A | 2/1997 | Sargent et al. |
| 5,604,097 A | 2/1997 | Brenner |
| 5,620,854 A | 4/1997 | Holzrichter et al. |
| 5,666,190 A | 9/1997 | Quate et al. |
| 5,670,322 A | 9/1997 | Eggers et al. |
| 5,688,486 A | 11/1997 | Watson et al. |
| 5,720,928 A | 2/1998 | Schwartz |
| 5,744,305 A | 4/1998 | Fodor et al. |
| 5,753,088 A | 5/1998 | Olk |
| 5,760,300 A | 6/1998 | Kajimura |
| 5,763,768 A | 6/1998 | Henderson et al. |
| 5,789,167 A | 8/1998 | Konrad |
| 5,800,992 A | 9/1998 | Fodor et al. |
| 5,804,445 A | 9/1998 | Brasier |
| 5,837,832 A | 11/1998 | Chee et al. |
| 5,840,862 A | 11/1998 | Bensimon et al. |
| 5,846,724 A | 12/1998 | Bensimon et al. |
| 5,851,769 A | 12/1998 | Gray et al. |
| 5,866,328 A | 2/1999 | Bensimon et al. |
| 5,866,434 A | 2/1999 | Massey et al. |
| 5,874,219 A | 2/1999 | Rava et al. |
| 5,874,668 A | 2/1999 | Xu et al. |
| 5,965,133 A | 10/1999 | Cantor et al. |
| 5,981,733 A | 11/1999 | Gamble et al. |
| 5,985,356 A | 11/1999 | Schultz et al. |
| 5,992,226 A | 11/1999 | Green et al. |
| 5,993,627 A | 11/1999 | Anderson et al. |
| 6,004,617 A | 12/1999 | Schultz et al. |

(Continued)

FOREIGN PATENT DOCUMENTS

EP        1063287        12/2000

(Continued)

OTHER PUBLICATIONS

Lal et al., "Multimodal Atomic Force Microscopy: Biological Imaging Using Atomic Force Microscopy Combined with Light Fluorescence and Confocal Microsopies and Electrophysiologic Recording", International Journal of Imaging Systems and Technology, vol. 8, 293-300 (1997).*

(Continued)

*Primary Examiner*—Ann Y. Lam
(74) *Attorney, Agent, or Firm*—Michael Best & Friedrich LLP

(57) ABSTRACT

The interrogation of extremely small sample volumes can be accomplished with the present invention. Provided are probes having disposed thereon a plurality of domains forming an array, which is suitably a nanoarray. Also provided are methods of detecting molecules and molecular interaction events, retrieving and analyzing analytes, and delivering substances to cells or tissues using probes of the invention.

43 Claims, 6 Drawing Sheets

U.S. PATENT DOCUMENTS

| | | | |
|---|---|---|---|
| 6,024,925 | A | 2/2000 | Little et al. |
| 6,033,911 | A | 3/2000 | Schultz et al. |
| 6,045,671 | A | 4/2000 | Wu et al. |
| 6,080,586 | A | 6/2000 | Baldeschwieler et al. |
| 6,083,763 | A | 7/2000 | Balch |
| 6,087,274 | A | 7/2000 | Tonucci et al. |
| 6,110,426 | A | 8/2000 | Shalon et al. |
| 6,123,819 | A | 9/2000 | Peeters |
| 6,143,574 | A | 11/2000 | Karlsson et al. |
| 6,146,899 | A | 11/2000 | Porter et al. |
| 6,159,742 | A | 12/2000 | Lieber et al. |
| 6,171,797 | B1 | 1/2001 | Perbost |
| 6,180,114 | B1 | 1/2001 | Yager |
| 6,200,737 | B1 | 3/2001 | Walt et al. |
| 6,203,814 | B1 | 3/2001 | Fisher et al. |
| 6,210,910 | B1 | 4/2001 | Walt et al. |
| 6,214,552 | B1 | 4/2001 | Heroux et al. |
| 6,218,122 | B1 | 4/2001 | Friend et al. |
| 6,231,744 | B1 | 5/2001 | Ying et al. |
| 6,232,706 | B1 | 5/2001 | Dai et al. |
| 6,239,273 | B1 | 5/2001 | Pease et al. |
| 6,255,469 | B1 | 7/2001 | Seeman et al. |
| 6,270,946 | B1 | 8/2001 | Miller |
| 6,278,231 | B1 | 8/2001 | Iwasaki et al. |
| 6,284,497 | B1 | 9/2001 | Sabanayagam et al. |
| 6,287,850 | B1 | 9/2001 | Besemer et al. |
| 6,289,717 | B1 | 9/2001 | Thundat et al. |
| 6,309,831 | B1 | 10/2001 | Goldberg et al. |
| 6,325,904 | B1 * | 12/2001 | Peeters ................... 257/414 |
| 6,329,209 | B1 | 12/2001 | Wagner et al. |
| 6,331,396 | B1 | 12/2001 | Silverman |
| 6,346,189 | B1 | 2/2002 | Dai et al. |
| 6,350,609 | B1 | 2/2002 | Morozov et al. |
| 6,395,554 | B1 | 5/2002 | Regan et al. |
| 6,395,562 | B1 | 5/2002 | Hammock et al. |
| 6,406,921 | B1 | 6/2002 | Wagner et al. |
| 6,416,952 | B1 | 7/2002 | Pirrung et al. |
| 6,420,105 | B1 | 7/2002 | Landfield et al. |
| 6,436,647 | B1 | 8/2002 | Quate et al. |
| 6,518,168 | B1 | 2/2003 | Clem et al. |
| 6,573,369 | B2 | 6/2003 | Henderson et al. |
| 6,635,311 | B1 | 10/2003 | Mirkin et al. |
| 6,722,395 | B2 | 4/2004 | Overbeck |
| 7,195,872 | B2 * | 3/2007 | Agrawal et al. ............. 435/6 |
| 2001/0044106 | A1 | 11/2001 | Henderson et al. |
| 2002/0042081 | A1 | 4/2002 | Henderson et al. |
| 2002/0063212 | A1 | 5/2002 | Mirkin et al. |
| 2002/0076927 | A1 | 6/2002 | Henderson et al. |
| 2002/0114987 | A1 | 8/2002 | Oscarsson et al. |
| 2002/0122873 | A1 | 9/2002 | Mirkin et al. |
| 2002/0123135 | A1 | 9/2002 | Henderson et al. |
| 2002/0146714 | A1 | 10/2002 | Lieber et al. |
| 2002/0164656 | A1 | 11/2002 | Hoeffler et al. |
| 2002/0172943 | A1 | 11/2002 | Henderson et al. |
| 2002/0179434 | A1 | 12/2002 | Dai et al. |
| 2003/0013111 | A1 | 1/2003 | Henderson et al. |
| 2003/0228695 | A1 | 12/2003 | Nakamura et al. |

FOREIGN PATENT DOCUMENTS

| | | |
|---|---|---|
| JP | 6124680 | 5/1994 |
| JP | 7027771 | 1/1995 |
| JP | 8094646 | 4/1996 |
| WO | WO 92/15709 | 9/1992 |
| WO | WO 96/31775 | 10/1996 |
| WO | WO 97/06420 | 2/1997 |
| WO | WO 97/18326 | 5/1997 |
| WO | WO 98/05920 | 2/1998 |
| WO | WO 98/18959 | 5/1998 |
| WO | WO 99/31267 | 6/1999 |
| WO | WO 99/44063 | 9/1999 |
| WO | WO 00/04382 | 1/2000 |
| WO | WO 00/04389 | 1/2000 |
| WO | WO 00/04390 | 1/2000 |
| WO | WO 00/36136 | 6/2000 |
| WO | WO 00/41213 | 7/2000 |
| WO | WO 00/46406 | 8/2000 |
| WO | WO 01/60316 | 8/2001 |
| WO | WO 01/91855 | 12/2001 |
| WO | WO 02/31183 | 4/2002 |
| WO | WO 03/001633 | 1/2003 |
| WO | WO 03/036767 | 5/2003 |
| WO | WO 03/038033 | 5/2003 |
| WO | WO 03/048314 | 6/2003 |
| WO | WO 03/052514 | 6/2003 |

OTHER PUBLICATIONS

Tamayo et al., "Chemical sensors and biosensors in liquid environment based on microcantilevers with amplified quality factor", Ultramicroscopy) (2001) 1-7.*

Yan et al., "A general microcantilever surface modification using a multilayer for biospecific recognition", Organic and Biomolecular Chemistry, available on-line (2002).*

"Microbeam Mass Spectrometry" Chemical Science and Technology Laboratory, Surface and Microanalysis Science Division http://www.cstl.nist.gov/div837/Divisoin/expertise/ions/masspec1.htm Jul. 18, 2002.

Abstracts of Papers Part I, 214th "Abstract 027" *ACS National Meeting American Chemical Society*, Sep. 1997, 2 pgs.

Allison, D., et al., "Direct atomic force microscopy imaging of *Eco*RI endonuclease site specifically bound to plasmid DNA molecules" *PNAS USA*, 1996, 93:8826-8829.

Allison, D., et al., "Mapping Individual Cosmid DNAs by Direct AFM Imaging" *Genomics*, 1997, 41:379-384.

Alves, et al., Atomic scale imaging of alkanethiolate monolayers at gold surfaces with atomic force microscopy: *J. Am. Chem. Soc.*, Feb. 1992, 114(4):1222-1227.

Amro, et al., "Patterning surfaces using tip-directed displacement and self-assembly" *Langmuir*, 2000, 16:3006-3009.

Anwander, et al., "Surface characterization and functionalization of MCM-41 silicas via silazane silylation" *J. Phys. Chem. B.*, 2000, 104:3532-3544.

Arntz, et al., "Label-free protein assay based on a nanomechanical cantilever array" *Nanotechnology*, 14 (2003) 86-90.

Ausubel, F.M., et al. "Current Protocols in Molecular Biology" 1993 ed. vol. 1&2, 1993, Green Publishing Associates and Wiley-Interscience.

Bailey, C.P., et al., Cationic oligonucleotides can mediate specific inhibition of gene expression in *Xenopus oocytes Nuc. Acids Res.*, 1998, 26(21):4860-4867.

Bain, et al., "Modeling organic surfaces with self-assembled monolayers" *Agnew. Chem. Int. Ed. Engl.*, 1989, 28(4):506-512.

Baselt, D.R., et al., "A biosensor based on magnetoresistance technology" *Biosens. Bioelectorn*, 1998, 13(7-8):731-739.

Bedouelle, H., "Reagentless fluorescent Immunosensors" *Antibody Engineering*, IBC's 13th International Conference, Dec. 2, 2002.

Belaubre, P. et al., "Fabrication of biological microarrays using microcantilevers". *Applied Physics Letters,.* May 5, 2003, 82(18):3122-3124.

Bensimon, A., et al., "Alignment and sensitive detection of DNA by a moving interface" *Science*, Sep. 30, 1994; 265(5181):2096-2098 [PMID 7522347] Abstract.

Berggren, et al., "Microlithography by using neutral metastable atoms and self-assembled monolayers" *Science*, Sep. 1995, 269(5228):1255-1257.

Bernard, et al. "Printing patterns of proteins" *Langmuir The ACS Journal of Surfaces and Colliod*, Apr. 1998, 14(9):2225-2229.

Binggeli, et al., "Influence of capillary condensation of water on nanotribology studied by force microscopy" *Appl. Phys. Lett.*, Jul. 1994, 65(4):415-417.

Binning, et al., "Surface studies by scanning tunneling microscopy" *Phys. Rev. Lett.*, 1982, 49(1):57-61.

Binning, G., et al., Atomic force microscope *Phys. Rev. Lett.*, 1986, 56(9):930-933.

Bishop, et al., "Self-assembled monolayers: recent developments and applications" *Colloid & Interface Science*, Feb. 1996, 1:127-136.

Bottomley, L., "Scanning probe microscopy" *Anal. Chem.*, Jun. 1998, 70(12):425R-475R.

Brandow, S., et al., "Metal pattern fabrication using the local electric field of conducting atomic force microscope probe" *J. Vac. Sci. Technol.*, May/Jun. 1997, 15(3):1455-1459.

Brenner, S., et al., "Gene expression analysis by massively parallel signature sequencing (MPSS) on microbead arrays" *Nat. Biotechnol 2000*, Jun. 18(6):630-634, 2000.

Brody, E., and Gold, L., "Aptamers as therapeutic and diagnostic agents" *Molecular Biotechnology*, 2000, 74:5-13.

Bruckbauer, et al., "Writing with DNA and Protein Using a Nanopipet for Controlled Delivery" *JACS*, 2002, A-B.

Bulyk, et al., "Quantifying DNA-protein interactions by double-stranded DNA arrays" *Nature Biotechnology*, Jun. 1999, 17:573-577.

Busch, K.L., "Desorption Ionization Mass Spectrometry," *J. Mass Spectrometry* (1995) 30:233-240.

Bustamante C., et al., "Circular DNA Molecules Imaged in Air by Scanning Force Microscopy" *Biochemistry*, 1992, 31:22-26.

Bustamante, C., et al., "Biochemical and structural applications of scanning force microscopy" *Curr. Opin. Struct. Biol.*, 1994 4(5):750-760.

Carr, et al., "High-selectivity pattern transfer process for self-assembled monolayer electron beam resists" *J. Vac. Sci. Technol.*, May/Jun. 1997, 15(3):1446-1450.

Cheng, et al., "Preparation and hybridization analysis of DNA/RNA from E. coli on microfabricated bioelectronic chips" *Nature Biotechnology*. 1998, 16:541-546.

Chrisey et al, "Fabrication of patterned DNA surfaces" *Nucleic Acids Research*, (Oct. 1996)24(15):3040-3047.

Clark, M.W. et al., "Nanotechnology tools for functional proteomics analysis" *American Biotechnology Laboratory*, Mar. 2001, 16-18.

Colas, et al., "Genetic selection of peptide aptamers that recognize an inhibit cyclin-dependent kinase 2", *Nature*, Apr. 1996 380(11):548-550.

Collins, et al., "Engineering Carbon Nanotubes and Nanotube Circuits Using Electrical Breakdown" *Science*, Apr. 2001, 292(5517):706-799.

Collins, et al., "Nanotube Device" *Science*, Oct. 3, 1997, 278:100-103.

Colvin, et al., "Semiconductor nanocrystals covalently bound to metal surfaces with self-assembled monolayers" *J. Am. Chem. Soc.*, 1992, 114:5221-5230.

Cui, Y, et al., "Nanowire nanosensors for highly sensitive and selective detection of biological and chemical species" *Science*, 2001, 293, 1289-1292.

Dai, H, et al., "Controlled chemical routes to nanotube architectures" Physic and Devices, *J. Phys. Chem B*, 1999, 103:11246-11255.

Dai, H, et al., "Probing electrical transport in nanomaterials: conductivity of individual carbon nanotubes" *Science*, 1996, 272(5261):523-526.

Dammer, et al., "Binding strength between cell adhesion proteoglycans measured by atomic force microscopy" *Science*, 1995, 267:1173-1175.

Dammer, et al., "Specific antigen/antibody interactions measured by force microscopy" *Biophys. J.*, 1996, 70:2437-2441.

Delamarche, E., "Immobilization of antibodies on a photoactive self-assembled monlayer on gold," *Langmuir* (1996) 12:1997-2006.

Ding, Y., Oka, T., et al., "Near-field stimulated TOF nanometric surface mass spectroscopy: characterization of Nano-localized surfaces" Joint International Meeting—200th Meeting of the Electrochemical Society, Inc., 52nd Annual Meeting of the International Society of Electrochemistry, San Francisco, California (2001).

Ding, Y., Ruggero, M. et al., "Development of UHV-STM/TOF hybrid mass analyzer system for nano-characterization of metal silicide surfaces" 198th Meeting of the Electrochemical Society, Phoenix, Arizona (2000).

DeRisi, et al., "Exploring the Metabolic and Genetic Control of Gene Expression on a Genomic Scale" *Science*, Oct. 1997, 278:680-686.

Dong, Y. and Shannon, C., "Heterogeneous Immunosensing Using Antigen and Antibody Monolayers on Gold Surfaces with Electrochemical and Scanning Probe Detection" *Anal. Chem.*, 2000, 72:2371-2376.

Dontha, N., et al., "Development of sub-micron patterned carbon electrodes for immunoassays" *J. Pharm. Biomed. Analysis*, (Feb. 1999) 19:83-91.

Dontha, N., et al., "Generation of Biotin/Avidin/Enzyme Nanostructures with Maskless Photoligography" *Anal. Chem.*, 1997, 69: 619-2625.

Dubois, L. et al., "Synthesis, Structure, and Properties of Model Organic Surfaces" *Annu. Rev. Phys. Chem.*, 1992, 43:437-463.

Durbin, S., Feher, G., "Protein crystallization" *Annual Review of Phys Chemistry*. 1996, 47:171-204.

Falvo, M.R., et al., "Bending and buckling of carbon nanotubes under large strain" *Nature*, 1997, 389:582-584.

Fan, S., et al., "Self-oriented regular arrays of carbon nanotubes and their functional devices" *Science*, 1999, 283, 512.

Fang, et al., "Membrane Protein Microarrays" *JACS*. 2002, 124(11):2394-2395.

Farajian, A.A., et al., "Nonlinear Coherent Transport Through Doped Nanotube Junctions" *Physical Review*, Jun. 21, 1999, 82(25):5084-5087.

Feigon, J. "DNA triplexes, quadruplexe, and aptamers" *Clin. Chem.*, 1994, 40(4):647-647.

Florin, E., et al., "Adhesion forces between individual ligan-receptor pairs" *Science*, 1994, 264:415-417.

Fodor, S., et al., "Light-directed spatially addressable parallel chemical synthesis" *Science* 1991, 251:767-773.

Fodor, S., et al., "Multiplexed biochemical assays with biological chips" *Nature*, 1993, 364:555-557.

Frisbie, C.D., et al., "Functional group imaging by chemical force microscopy" *Science*, 1994, 265:2071-2074.

Fritz, J., et al., "Translating biomolecular recognition into nanomechanics" *Science*, 2000, 316-318.

Fritzsche, W., et al., "Application of Atomic Force Microscopy to Visualization of DNA, Chromatin and Chromosomes" *Critical Reviews™ in Eukaryotic Gene Expression*, 1997, 7(3):231-240.

Fritzsche, W., et al., "Chicken Erythrocyte Nucleosomes Have a Defined Orientation along the Linker DNA-A Scanning Force Microscopy Study" *Scanning*, 1997, 19:42-47.

Fritzsche, W., et al., "Mapping elasticity of rehydration metaphase chromosomes by scanning force microscopy" *Ultramicroscopy*, 1997, 69:191-200.

Fritzsche, W., et al., "Ribosome substructure investigated by scanning force microscopy and image processing" *Journal of Microscopy*, 1998, 189, Pt 1, 50-56.

Fuhrer, et al., "Crossed Nanotube Junctions" *Science*, Apr. 21, 2000, 288:494-497.

Fujihira, et al., "Effect of capillary force on friction force microscopy: a scanning hydrophilicity microscope" *Chemistry Letters*, Jul. 1996, 7:499-500.

Gantzer, C. et al., "Detection of infectious enteroviruses, enterovirus genomes, somatic coliophages, and bacteroides fragilis phages in treated wastewater," *Appl. Environ. Microbiol.* (1998) 64:4307-4312.

Gauntt, C. and Huber, S., *Front Biosci.* (2003) 8:E23.

Gillen, G., Bennett, J., et al., "Molecular imaging secondary ion mass spectrometry for the characterization of patterned self-assembled monolayers on silver and gold" *Anal. Chemistry*, 1994, 66:2170-2174.

Girault, S., Chassaing, G. et al, "Coupling of MALDI-TOF mass analysis to the separation of biotinylated peptides by magnetic streptavidin beads" *Anal. Chemistry* 1996, 68:2122-2126.

Grabar, et al., "Preparation and characterization of Au colloid monolayers" *Anal. Chem.*, 1995, 67(4):735-743.

Haab, et al., "Protein microarrays for highly parallel detection and quantitation of specific proteins and antibodies in complex solutions" *Genome Biology*, 2001, 2(2)0004.1-0004.13.

Hansma, H.G., et al., "Atomic force microscopy of long and short double-stranded, single-stranded and triple-stranded nucleic acids" *Nuc. Acids Res.*, 1996, 24(4):713-720.

Hansma, H.G., et al., "Recent advances in atomic force microscopy of DNA" *Scanning* 1993, 15(5):296-9.

Hansma, H.G., Sinsheimer, R.L., et al., "Atomic force microscopy of single- and double-stranded DNA" *Nucleic Acids Research* 1992, 20:3585-90.

Hansma, P.K., et al., "Tapping mode atomic force microscopy in liquids" *Appl. Phys. Lett.*, 1994, 64(13):1738-1740.

Heller, et al., "Discovery and analysis of inflammatory disease-related genes using cDNA microarrays" *PNAS USA*, 1997, 94: 2150-2155.

Henderson, E., "Atomic force microscopy of conventional and unconventional nucleic acid structures" *Journal of Microscopy*, 1992, 77-84.

Henderson, E., "Imaging and nanodissection of individual supercoiled plasmids by atomic force microscopy" *Nuc. Acids Res.*, 1992, 20(3):445-447.

Henderson, E., "Imaging of Living Cells by Atomic Force Microscopy" *Progress in Surface Science*, May 1994, 46(1):39-60.

Henderson, E., "Molecular force detection and spectroscopy with the atomic force microscope" *Science Progress*, 1998, 81(2):141-151.

Henderson, E., et al., "Actin Filament Dynamics in Living Glial Cells Imaged by Atomic Force Microscopy" *Science*, 1992, 257:1944-1946.

Henderson, E., et al., "New Ribosome Structure" *Science*, 1984, 255:510-512.

Henderson, E., et al., "Telomeric DNA oligonucleotides form novel intramolecular structures containing guanine-guanine base pairs" *Cell*, 1987, 51(6):899-908.

Henderson, et al., "A method for gold coating experimental detector beampipes" httb://www.lns.cornell.edu/public/CBN/1999/CBN99-7/cbn99-7.pdf, 1999.

Hiller, et al., "Microarrayed allergen molecules: diagnostic gatekeepers for allergy treatment" FASEB, 2002, 16:414-416.

Hinterdorfer, P. et al., "Detection and localization of individual antibody-antigen recognition events by atomic force microscopy" *PNAS*, 1996, 93:3477-3481.

Hoh, J.H., and Hansma, P.K., "Atomic force microscopy for high resolution imaging in cell biology" *Trends in Cell Biology*, 1992, 2:208-213.

Hoh, J.H., et al., "Atomic force microscopy and dissection of gap junctions" *Science*, 1991, 1405-1408.

Hoh, J.H., et al., "Quantized adhesion detected with the atomic force microscope" *J. Am. Chem. Soc.*, 1992, 114:4917-4918.

Holland, Vacuum Deposition Of Thin Films (Wiley, New York, NY, 1956).

Hong, et al., "A new tool for studying the in situ growth processes for self-assembled monolayers under ambient conditions" *Langmuir*, 1999, 15:7879-7900.

Hong, et al., "Multiple ink nanolithography: toward a multiple-pen nano-plotter" *Science*, 1999, 286:523-525.

Hong, S. et al. "A Nanoplotter with Both Parallel and Serial Writing Capabilities" *Science*, Jun. 9, 2000, 288:1808-1811.

Hovis, et al., "Cyloaddition chemistry and formation of ordered organic monolayers on silicone (001) surfaces" *Surface Science*, 1998, 402-404, pp. 1-7.

Hovis, et al., "Structure and bonding of ordered organic monolayers of 1,5-cyclooctadiene on the silicon (001) Surface" *J. Phys. Chem. B.*, 1997, 101: 9581-9585.

Hu, et al., "Imaging the condensation and evaporation of molecularly thin films of water with nanometer resolution" *Science*, 1995, 268(5208):267-269.

Huck, et al., "Patterned polymer multilayers as etch resists" *Langmuir*, 1999, 15:6862-6867.

Ivanisevic, et al., "Dip-Pen Nanolithography on Semiconductor Surfaces" *J. Am. Chem. Soc.*, 2001, 123:7887-7889.

Iyer, et al., "The Transcription Program in the Response of Human Fibroblasts to Serum" *Science*, 1999, 283(5398):83-87.

Jackman, et al., "Fabrication of submicrometer features on curved substrates by microcontact printing" *Science*, 1995, 269: 664-666.

James, et al., "Patterned protein layers on solid substrates by thin stamp microcontact printing" *Langmuir*, 1998, 14:741-744.

Janes, et al., "Electronic conduction through 2D arrays of nanometer diameter metal clusters" *Superlattices and Microstrucures*, 1995, 18(4):275-282.

Jaschke, et al., "Deposition of organic material by the tip of a scanning force microscope" *Langmuir*, 1995, 11:1061-1064.

Jin, X., Unertl, W., "Submicrometer modification of polymer surfaces with a surface force microscope" *Applied Physics Letters*, 1992, 61(6): 657-659.

Jones, V., et al., "Microminiaturized Immunoassays Using Atomic Force Microscopy and Compositionally Patterned Antigen Arrays 66" *Anal. Chem.*, 1998, 70(7):1233-1241.

Karpovich, et al., "Direct measurement of the adsorption kinetics of alkanethioilate self-assembled monolayers on microcrystalline gold surface" *Langmuir*, 1994, 10:3315-3322.

Kim, et al., "Nanotube nanotweezers" *Science*, Dec. 10, 1999, 286:2148-2150.

Knezevic et al., "Proteomic profiling of the cancer microenvironment by antibody arrays" *Proteomics*, 2001,. 1:1271-1278.

Kochanek, et al., "Transcriptional silencing of human ALU sequences and inhibition of protein binding in the box B regulatory elements by 5'CG3" methylation" *FEBS Lett.*, 1995, 360(2):115-120 [PMID 7875314] Abstract.

Komeda, et al., "Octadecyltrichlorosilane self-assembled-monolayer islands as a self-patterned-mask for HF etching of $SiO_2$ on Si" *J. Vac. Sci. Technol A.*, 1998, 16(3):1680-1685.

Kong, et al., "Nanotube Molecular Wires as Chemical Sensors" *Science*, Jan. 28, 2000, 287:622-625.

Kumar, et al., "The use of self-assembled monolayers and a selective etch to generate patterned gold features" *J. Am. Chem. Soc.*, 1992, 114:9188-9189.

Lahiri, et al., "Patterning ligands on reactive SAMs by microcontact printing" *Langmuir*, 1999, 15:2055-2060.

Laibinis et al., "a-terminated alkanethiolate monolayers on surfaces of copper, silver, and gold have similar wettabilities[1]" *J. Am. Chem. Soc.*, 1992, 114: 1990-1995.

Lal, R. and John, S.A., "Biological applications of atomic force microscopy" *Am J. Physiology.* 1994, 266(1):1-21.

Lanio, T., et al., "PCR-based random mutagenesis method using spiked oligonucleotides to randomize selected parts of gene without any wild-type background" *Biotechniques*, 1998, 25(6):958-965.

Lee, et al., "Nanometer-scale lithography on H-passivated Si(100) by atomic force microscope in air" *J. Vac. Sci. Technol. A.*, 1997, 15(3):1451-1454.

Lee, G. et al. "Direct measurement of the forces between complementary strands of DNA" *Science*, 1994, 266:771-773.

Lercel, et al. "Self-assembled monolayer electron-beam resists on GaAs and $SiO_2$" *J. Vac. Sci. Technol. B.*, 1993, 11(6): 2823-2828.

Lercel, et al., "Sub-10nm lithography with self-assembled monolayers" *Appl. Phys. Lett.*, 1996, 68(11):1504-1506.

Li, Y. et al., "Electrochemical AFM "Dip-Pen" Nanolithography" *J. Am. Chem., Soc.* 2001, 123:2105-2106.

Liu, et al., "Nanofabrication of self-assembled monolayers using scanning probe lithography" *Acc. Chem. Res.*, 2000, 33(7):457-466.

Lo, et al., "Organic and inorganic contamination on commercial AFM cantilevers" *Langmuir*, 1999, 15:6522-6526.

Lüthi, et al., "Parallel nanodevice fabrication using a combination of shadow mask and scanning probe methods: *Applied Physics Letters*, 1999, 75(9):1314-1316.

Lutwyche, et al., "5X5 2D AFM cantilever arrays a first step toward Terabit storage device" *Sensors and Actuators*, 1999, 73:89-94.

Lynch, M., et al., "A Reliable Preparation Method for Imaging DNA by AFM" *Microscopy Today*, 1999, 99(9) 1 pg.

Lyubchenko, Y.L., et al., "Atomic force microscopy of DNA and bacteriophage in air, water and propanol: The role of adhesion forces"*Nuc. Acids Res.*, 1993, 21(5):1117-1123.

Macaya, et al., "Thrombin-binding DNA aptamer forms a unimolecular quadruplex structure in solution" *PNAS USA*, Apr. 1993, 90:3745-3749.

MacBeath, G. and Schreiber, S.L., "Printing Proteins as Microarrays for High-Throughput Function Determination" *Science*, Sep. 8, 2000, 289:1760-1763.

Magno, R., Bennett, B., "Nanostructure patterns written in III-V semiconductors by an atomic force microscope" *Applied Physics Letters*, 1997, 70(14):1855-1857.

Malmborg, et al., "Real Time Analysis of Antibody-Antigen Reaction Kinetics", *Scand. J. Immunol.*, 1992, 35:634-650.

Marsh, T.C., et al., "A new DNA nanosctructure imaged by scanning probe microscopy" *Nuc. Acids Res.* 1995, 23(4):696-700.

Marsh, T.C., et al., "G-wires: Self-assembly of a telometic oligonucleotide, d(GGGGTTGGGG), into large superstructures" *Biochemistry* 1994, 33:10718-10724.

Martin, B., et al., "Ortogonal Self-Assembly on Colloidal Gold-Platinum Nanorods" *Advanced Materials*, 1999, 11:1021.

Matteucci, et al., "Synthesis of deoxyoligonucleotides on a polymer support 1" *J. Am. Chem. Soc.*, 1981, 103:3185-3191.

Maynor, et al., "Au :Ink" for AFM "Dip-Pen" Nanolithography *Langmuir*, 2001, 17:2575-2579.

Mazzola, L., "Discrimination of DNA hybridization using chemical force microscopy" *Biophysical Journal*, 1999, 76:2922-2933.

Mazzola, L., "Imaging biomolecule arrays by atomic force microscopy" *Biophysical Journal*, 1995, 68:1653-1660.

Meister, et al., "Nanoscale Dispensing of Liquids through Cantilevered Probes" *MNE '02*, Lugano, Switzerland, Sep. 16-19, 2002.

Mendoza, et al., "High-Throughput Microarray-Based Enzyme-Linked Immunosorbent Assay (ELISA)" *BioTechniques*, 1994, 27(4):778-788.

Meyer, G. and N.M. Amer, "Novel optical approach to atomic force microscopy" *Appl. Phys. Lett.*, 1988, 53:1045-1047.

Minne, et al., "Centimeter scale atomic force microscope imaging and lithography" *Applied Physics Letters*, 1998, 73(12):1742-1744.

Minne, S.C., et al., "Automated parallel high-speed atomic force microscopy" *Appl. Phys. Lett.*, 1998, 72(18):2340-2342.

Mirkin, et al., "Dip-Pen Nanolithography: Controlling Surface Architecture on the Sub-100 Nanometer Length Scale" *Chemphyschem*, 2001, 2:37-39.

Mirkin, et al., "Programming the Assembly of Two- and Three-Dimensional Architectures with DNA and Nanoscale Inorganic Building Blocks" Invited Contribution from Recipient of ACS Award in Pure Chemistry *Inorg. Chem.*, 2000, 39:2258-2272.

Mosher, C., et al., "NanoArrays, The Next Generation Molecular Array Format for High Throughput Proteomics, Diagnostics and Drug Recovery" *JALA*, 2000, 5(5):75-83.

Moy, et al., "Intermolecular Forces and Energies Between Ligands and Receptors" *Science*, 1994, 266:257-259.

Moy, V.T., et al., "Probing the forces between complimentary strands of DNA with the atomic force microsope" *SPIE*, 1995, 2384:2-12.

Mueller, et al., "Atomic force microscopy depostition of poly-l-lysine structures onto lipid bilayers supported by mica" *Langmuir*, 2000, 16:9568-9570.

Müller, et al., "Nanostructuring of alkanethiols with ultrastrap field emitters" *J. Vac. Sci. Technol. B.*, 1995, 13(6):2846-2849.

Murray, et al., "Atomic force microscopy of biochemically tagged DNA" *Proc., Natl., Acad. Sci.*, 1993, 90:3811-3814.

Musil, C., Nanostructuring of gold electrodes for immunosensing applications: *J. Vac. Sci. Technol. B.*, 1995, 13(6):2781-2786.

Niu, et al., "Atomic force microscopy of DNA-colloidal gold and DNA-protein complexes" *SPIE Advances in DNA Sequencing Technology*, 1993, 1891:71-77.

Noy, et al., "Chemical force microscopy: exploiting chemically-modified tips to quantify adhesion, friction, and functional group distributions in molecular assemblies" *J. Am. Chem.*, 1995, 117:7943-7951.

Noy, et al., "Chemically-sensitive imaging in tapping mode by chemical force microscopy: relationship between phase lag adhesion" *Langmuir*, 1998, 14:1508-1511.

Nuzzo, R., "Spontaneously organized molecular assemblies. 3. Preparation and properties of solution adsorbed monolayers of organic disulfides on gold surfaces" *J. Am. Chem. Soc.*, 1987, 109:2358-2368.

Nyffenegger, et al., "Nonometer scale surface modification using the scanning probe microscope: progress since 1991" *Chem. Rev.*, 1997, 97:1195-1230.

O'Brien, J., et al., "Immunosensing Platforms Using Spontaneously Absorbed Antibody Fragments on Gold" *Analytical Chemistry*, 2000, 72(4)703-710 [PMID 10701253] Abstract.

Oshio, T. et al., "Atomic force microscopy detection system using an optical fiber heterodyne interferometer free from external disturbances" *Ultramicroscopy* 42-44 (Jul. 1992) 310-314.

Paweletz, et al., "Reverse phase protein microarrays which capture disease progression shoe activation of pro-survival pathways at the cancer invasion front" *Oncogen*, 2001, 20:1981-1989.

Pawlak, et al., "Zeptosens' protein microarrays: A novel high performance microarray platform for low abundance protein analysis" *Proteomics*, 2002,. 2:383-393.

Perkins, et al., "Fabrication of 15 nm wide trenches in Si by vacuum scanning tunneling microscope lithography of an organosilane self-assembled film and reactive ion etching" *Appl. Phys. Lett.*, 1996, 68(4):550-552.

Pfannschmidt, et al., "Sequence-specific labeling of superhelical DNA by triple helix formation and psoralen crosslinking" *Nucleic Acids Research*, 1996 24(9):1702-1709.

Piner, et al., "Improved imaging of soft materials with modified AFM tips" *Langmuir*, 1999, 15:5457-5460.

Piner, R.D., et al., "Dip-Pen Nanolithography" *Science*, Jan. 29, 1999,283(5402):661-663.

Piner, Richard, "Effect of water on lateral force microscopy in air" *Langmuir*, 1997, 13:6864-6868.

Putnam, C.A.J., "Tapping atomic force microscopy in liquids" *Appl. Phys. Lett.*, 1994, 64(18):2454-2456.

Qin, et al., Fabrication of ordered two-dimensional arrays of micro- and nanoparticles using patterned self-assembled monolayers as templates: *Adv. Matter*, 1999, 11(17):1433-1437.

Rankin, P.C. Wilson, A.T. "The Surface Chemistry of the Mica-Aluminum-Sulfate System" *Journal of Colloid and Interface Science*, (1969) 30(3):277-282.

Reed, et al., "Conductance of molecular junction" *Science*, 1997, 278:252-254.

Rief, et al., "Reversible unfolding of individual Titin Ig-domains by AFM" *Science*, 1997, 276:1109-1111.

Rief, M., et al., "Single Molecule Force Spectroscopy on Polysaccharides by Atomic Force Microscopy" *Science*, 1997, 275:1295-1297.

Rief, M., et al., "The mechanical stability of immunoglobulin and fibronectin III domains in the muscle protein titin measured by atomic force microscopy" *Biophysical Journal*, 1998, 3008-3014.

Robinson, et al., Autoantigen microarrays for multiplex characterization of autoantibody responses *Nature Medicine*, Mar. 2002, 8(3):1-7.

Santos, et al., "Probing hydrophobic interactions of surfaces and macromolecules with atomic force microscope" *Book of Abstracts*, 214 ACS National meeting, Sep. 7-11, 1997, PHYS-248.

Sastry, et al., "Formation of patterned hetrocolloidal nanoparticle thin films" *Langmuir*, 2000, 16:3553-3556.

Schaus, S., et al., "Cell Viability and Probe-Cell Membrane Interactions of XRI Glial Cells Imaged by Atomic Force Microscopy" *Biophysical Journal*, Sep. 1997, 73:1205-1214.

Schena, et al., "Parallel human genome analysis : Microarray-based expression monitoring of 1000 genes" *PNAS USA*, 1996, 93:10614-10619.

Schena, M., *Microarray Biochip Technology*, Eaton Publishing, Natick, MA 2000.

Schoer, et al., "Scanning probe lithography. 4. Characterization of scanning tunneling microscope-induced patterns in *n*-Alknethiol self-assembled monolayers" *Langmuir*, 1997, 13:2323-2332.

Schumacher, et al., "Nanomachining of mesoscopic electronic devices using an atomic force microscope" *Applied Physics*, 1999, 75(8):1107-1109.

Schwartz, et al. "Meniscus Force Nanografting: Nanoscopic Patterning of DNA" *Langmuir*, 2001, 17:5971-5977.

Schwartz, et al., "Molecular Transport from an Atomic Force Microscope Tip: A Comparative Study of Dip-Pen Nanolithography" *Langmuir*, American Chemical Society, Nov. 6, 2001.

Schweitzer, et al., "Multiplexed protein profiling on microarrays by rolling-circle amplification" *Nature Biotechnology*, Apr. 2002, 20:359-365.

Shaiu, W.L., et al., "Atomic Force Microscopy of Oriented Linear DNA Molecules Labeled with 5nm Gold Spheres" *Nuc. Acids Res.*, 1993, 21(1):99-103.

Shaiu, W.L., et al., "Visualization of circular DNA molecules labeled with colloidal gold spheres using atomic force microscopy" *J. Vac. Sci. Technol. A.*, 11(4):820-823.

Sheehan, et al., "Thiol diffusion and the role of humidity in "dip pen"nanolithography" *Physical Review Letters*, Apr. 15, 2002, 88(15):156104-1-156104-4.

Sheen, et al., "A new class of organized self-assembled monolayers: alkane thiols on GaAs (100)" *J. Am. Chem. Soc.*, 1992, 114:1514-1515.

Sherman, Chemical Vapor Deposition For Microelectornices: Principles, Technology and Applications (Noyes, Park Ridges, NJ, 1987).

Shlyakhtenko, L.S., et al., "Structure and dynamics of supercoil-stabilized DNA cruciforms" *J. Mol. Biol.*, 1998, 280(1):61-72.

Shlyakhtenko, L.S., Gall, A.A., et al., "Atomic force microscopy imaging of DNA covalently immobilized on a functionalized mica substrate" *Biophysical Journal*, Jul. 1999, 77:568-576.

Silzel, et al., "Mass-sensing, multianalyte microarray immunoassay with imaging detection" *Clinical Chemistry*, 1998, 44(9):2036-2043.

Smith et al., "Overstretching B-DNA: the elastic response of individual double-stranded and single stranded DNA molecules" *Science*, Feb. 9, 1996, 271:795-799.

Snow, et al., "High speed patterning of a metal silicide using scanned probe lithography" *Applied Physics Letters*, 1999, 75(10):1476-1478.

Soh, H., et al., "Integrated nanotube circuits: controlled growth and ohmic contacts to single-walled-carbon nanotubes" *Appl. Phys. Letts.*, 1999, 75(5): 627-629.

Sondag-Huethorst, et al., "Generation of electrochemically deposited metal patterns by means of electron beam (nano)lithography of self-assembled monolayer resists" *Appl. Phys. Lett.* 1994, 64(3):285-287.

Southern, E.M., "Detection of specific sequences among DNA fragments separated by gel electrophoresis" *J. Mol. Biol.* 1975, 98:503-517.

Spectroscopy Europe—News Feb./Mar. 2002, 6 pages, http://www.spectroscopyeurope.com/news14_1.html.

Spence, J., Weierstall, U., et al., "Atomic species identification in scanning tunneling microscopy by time of flight spectroscopy" *J. Vac. Sci. Tech.*, 1996, B14(3):1587-1590.

Sreekumar, et al., "Profiling of cancer cells using protein microarrays: Discovery of novel radiation-regulated proteins" *Cancer Research*, 2001, 61:7585-7593.

Steiner, et al., "Adsorption of alkanenitriles and alkanedinitriles on gold and copper" *Langmuir*, 1992, 8:2271-2777.

Stöckle, R., Setz, P. "Nanoscale Atmospheric Pressure Laser Ablation-Mass Spectrometry" *Anal. Chem.*, 2001, 73(7):1399-1402.

Su, et al., "Moving beyond Molecules: Patterning Solid-State Features via Dip-Pen Nanolithography with Sol-Based Inks" *JACS*, 2002, 124(8):1560-1561.

Sun, et al., "Nanoscale Molecular Patterns Fabricated by Using Scanning Near-Field Optical Lithography" *JACS*, 2002, 124(11):2414-2415.

Tang, K., Fu, D., et al., "Matrix-assisted laser desorption/ionization mass spectrometry of immobilized duplex DNA probes" *Nucleic Acids Research*, 1995, 23(16):3126-3131.

Tans, et al., "Room-temperature transistor based on a single carbon nanotube" *Nature*, May 7, 1998, 393:49-52.

Tarlov, M.J., Newman, J.G., et al., "Static secondary ion mass spectrometry of self-assembled alkanethiol monolayers on gold" *Langmuir*, 1992, 8:1398-1405.

Tien, et al., "Microfabrication through electrostatic self-assembly" *Langmuir*, 1997, 13:5349-5355.

Troughton, E., Bain, C., et al., "Monolayer films prepared by the spontaneous self-assembly of symmetrical and unsymmetrical dialkyl sulfides from solution onto gold substrates: Structure, properties and reactivity of constituent functional groups" *Langmuir*, 1988, 4:365-385.

Tsukamoto, et al. "Twin-probe scanning tunneling microscope" *Rev. Sci. Instrum.*, Jul. 1991, 62(7):767-1771.

Uetz, P., et al., "A comprehensive analysis of protein-protein interactions in *Saccharomyces cerevisiae*" *Nature*, Feb. 10, 2000, 403(6770):623-627.

Ulman, Abraham, "Formation and structure of self-assembled monolayers" *Chem. Rev.*, 1996, 96:1533-1554.

Ulman, An Introduction To Ultrathin Organic Films: From Langmuir-Blodgett to Self-Assembly (Academic, Boston 1991) (Alkanethiols on gold).

Vesenka, J. et al., "A substrate preparation for reliable imaging of DNA molecules with the scanning force microscope" *Ultramicroscopy*. 1992, 42-44:1243-1249.

Vesenka, J., et al., "Colloidal gold particles as an incompressable atomic force microscope imaging standard for assessing the compressability of biomolecules" *Biophys. J.*, 1993, 65:992-997.

Vesenka, J., et al., "Combining optical and atomic force microscopy for life sciences research" *BioTechniques*, 1995, 19(2):240-253.

Vettiger, et al., "Ultrahigh density, high-data-rate NEMS-based AFM data storage system" *Microelectronic Engineering*. 1999, 46:11-17.

Vezenov, Dmitri, "Force titrations and ionization state sensitive imaging of functional groups in aqueous solutions by chemical force microscopy" *J. Am. Chem. Soc.*, 1997, 119:2006-2015.

Vossmeyer, et al., "Combinatorial approaches toward patterning nanocrystals" *Journal of Applied Pysics*, 1998, 84(7):3664.

Wadu-Mesthrige, et al., "Fabrication and imaging of nanomneter-sized protein patterns" *Langmuir*, 1999, 15:8580-8583.

Wallraff, et al., "Lithographic imaging techniques for the formation of nanoscopic features" *Chem. Rev.*, 1999, 99:1801-1821.

Walters, D.A., Hampton, A.D., et al. "Atomic force microscope integrated with a scanning electron microscope for the tip fabrication" *Applied Physics Letters*, Aug. 8, 1994, 65(6):787-789.

Wang, et al., "Nanometer scale patterning and pattern transfer on amorphous Si, crystalline Si, and $SiO_2$ surfaces using self-assembled monolayers" *Appl. Phys. Lett.*, 1997, 70(12):1593-1595.

Weierstall, U. Spense, J. "Atom species identification in STM using an Imaging Atom-Probe technique" *Surface Science* 1998, 398: 267-279.

Whitesides, et al., "Self-assembled monolayers and lithography" *Nanophase Chemistry* 1995, 39: 109-122.

Wilbur, et al., "Scanning force microscopes can image patterned self-assembled monolayers" *Langmuir*, 1995, 11:825-831.

Williamson, et al., "G-quartets in biology: Reprise" *PNAS USA*, Apr. 15, 1993, 90(8):3124-3124.

Williamson, et al., "Monovalent cation-induced structure of telomeric DNA: The G-quartet model" *Cell*, 1989, 59(5):871-880.

Wilson, et al., "Surface organization and nanopatterning of collagen by dip-pen nanolithography" *PNAS*, Nov. 20, 2001, 98(24):13660-13664.

Wong, S., et al., "Covalently functionalized nanotubes as nanometre-sized probes in chemistry and biolog" *Nature*, 1998, 394:52-55.

Wong, S., et al., "Covalently functionalized single-walled carbon nanotube probe tips for chemical force microscopy" *Journal of the American Chemical Society*, 1998, 120:8557-8558.

Wong, S., et al., "Functionalization of carbon nanotube AFM probes using tip-activated gases" *Chem Physics Letters*, 1999, 306:219-225.

Xia, et al., "A selective etching solution for use with patterned self-assembled monolayers of alkanethiolates on gold" *Chem. Mater.*, 1995, 7:2332-2337.

Xia, et al., "Complex optical surfaces formed by replica molding against elastomeric masters" *Science*, 1996, 273:347-349.

Xia, et al., "Pattern transfer: self-assembled monolayers as ultrathin resists" *Microelectronic Engineering*, 1996, 32:255-268.

Xia, et al., "Soft lithography" *Agnew Chem. Int. Ed.*, 1998, 37:551-575.

Xia, et al., "Unconventional methods for fabricating and patterning nanostructures" *Chem. Rev.*, 1999, 99:1823-1848.

Xu, et al., "Fabrication of nanometer scale patterns within self-assembled monolayers by nanografting" *Langmuir*, 1999, 15:7244-7251.

Xu, et al., Nanometer-scale fabrication by simultaneous nanoshaving and molecular self-assembly: *Langmuir*, 1997, 13:127-129.

Xu, et al., "Wetting and capillary phenomena of water on mica" *J. Phys. Chem. B.*, 1998, 102:540-548.

Yan, et al. "Patterning a performed, reactive SAM using microcontact printing" *J. Am. Chem. Soc.*, 1998, 120:6179-6180.

Yan, et al., "Patterning thin films of poly(ethylene imine) on a reactive SAM using microcontact printing" *Langmuir*, 1999, 15:1208-1214.

Ying, et al., "Programmable Delivery of DNA through a Nanopipet" *Anal. Chem.*, 2002, 74:1380-1385.

Youil, R., Screening for mutations by enzyme mismatch cleavage with T4 endonuclease VII *PNAS USA*, 1995, 92(1):87-91.

Zhong, Q., et al., "Fractured polymer/silica fiber surface studied by tapping mode atomic force microscopy" *Surf. Sci. Lett.*, Jan. 3, 1993, 290: L 688-L692.

Zhu, et al., "Analysis of yeast protein kinases using protein chips" *Nature Genetics*, 2000, 26:283-289.

Zhu, et al., "Global Analysis of Protein Activities Using Proteome Chips" *Science*, Sep. 2001, 293(14):2101-2105.

"FluoSpheres Fluorescent Microspheres—Product Information," Molecular Probes, Invitrogen Detection Technologies (2005) retrieved from the Internet: http://probes.invitrogen.com/media/pis/mp05000.pdf (XP-002378381).

Howland, R. et al., "A Practical Guide to Scanning Probe Microscopy," Thermomicroscopes (2002) retrieved from Internet: http://web.mit.edu/cortiz/www/AFMGallery/PracticalGuide.pdf (XP-002377197).

Li, S. et al., "Regression of tumors by IFN-α electroporation gene therapy and analysis of the responsible genes by cDNA array," Gene Therapy (2002) 9:390-397.

McKendry, R. et al., "Multiple label-free biodetection and quantitative DNA-binding assays on a nanomechanical cantilever array," PNAS (2002) 99(15):9783-9788.

Nishida, S. et al., "Combination of AFM with an objective-type total internal reflection fluorescence microscope (TIRFM) for nanomanipulation of single cells," Ultramicroscopy (2002) 91:269-274.

Oak Ridge National Laboratory, "Finding New Uses for Carbon Nanofibers," ORNL Review (2002) 35(3), retrieved from the Internet: http://www.ornl.gov/info/ornlreview/v35_3_02/improving.shtml (XP-002377196).

Pereira, R., "Atomic force microscopy as a novel pharmacological tool," Biochem. Pharma (2001) 62:975-983.

Vo-Dinh, T. et al., "Antibody-based nanoprobe for measurement of a fluorescent analyte in a single cell," Nature Biotech. (2000) 18:764-767.

Wu, G. et al., "Origin of nanomechanical cantilever motion generated from biomolecular interactions," PNAS (2001) 98(4):1560-1564.

\* cited by examiner

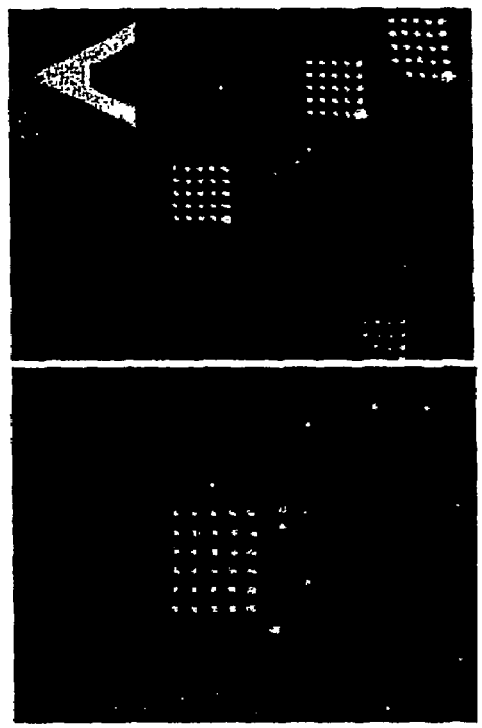
Figure 4. Antibodies printed on an AFM cantilever, then tagged with fluorescent secondary antibodies and visualized in a fluorescence microscope.

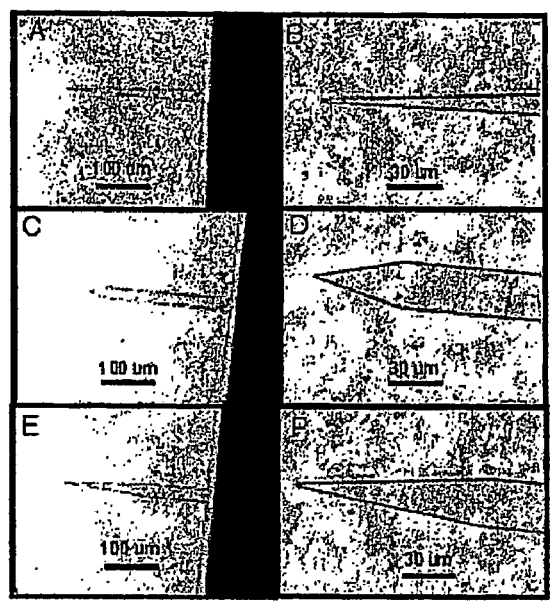
Figure 5. Brightfield images of microfabricated devices for practicing the invention. Key features of these devices is their size, on the same scale as a single cell, and their geometry, including sharp points or protrusions that act as cellular disruptors to facilitate penetration or disruption of cells or cellular components.

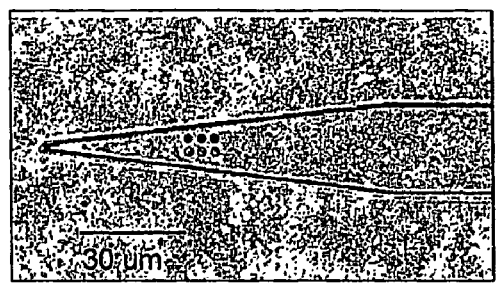
Figure 6. Two different antibody species printed on a device like that shown in Figure 5 in a 2 x 3 array.

METHOD AND APPARATUS FOR MOLECULAR ANALYSIS IN SMALL SAMPLE VOLUMES

CROSS-REFERENCE TO RELATED APPLICATIONS

This patent application is a national stage filing under 35 U.S.C. 371 of International Application No. PCT/US2003/041770, filed on Dec. 30, 2003, which claims priority to U.S. Provisional Patent Application No. 60/437,674, filed Jan. 2, 2003.

Understanding the nature of interactions between biomolecular and molecular species at both cellular and subcellular levels is key to the investigation of strategies for treating disease. One emerging methodology for elucidating the nature of molecular interactions involves the use of microarrays. Microarrays are spatially organized domains of various molecular species, and are typically constructed on solid supports arranged to facilitate rapid detection and characterization of molecular interaction events. Such events include interactions between biomolecules, antibodies and antigens, enzymes and substrates, and receptors and ligands, as well as biochemical and inorganic molecular events.

One benefit of microarray technology is the ability to provide a large number of test sites in a relatively small area. The size of the deposition domains, and in turn, the entire array, is of particular importance in determining the limits of sample volumes that can be tested.

There are four approaches for building conventional microarrays known in the art. These methods include mechanical deposition, in situ photochemical synthesis, "ink jet" printing and electronically driven deposition. Currently available mechanical deposition techniques produce domains of 25 to 100 microns in diameter or larger. In situ photochemical procedures allow for the construction of arrays of molecular species at spatial addresses in the 1-10 micron size range and larger. So-called "ink jet" methods produce domains in the 100 micron range. Electronic deposition can produce domains whose size is limited by the method used to construct the deposition electrode(s). Typically this is in the many micron diameter size range. However, cellular and sub-cellular molecular events take place in volumes many times smaller than the above-described available domain sizes. An apparatus and methods for interrogating extremely small sample volumes, would permit direct analyses of living cells in vivo or in situ.

Such arrays and methods would afford increased throughput and reduce the costs associated with array production and utilization. The arrays and methods would permit one to analyze extremely small sample volumes without requiring amplification of the material to be tested. A method of analyzing molecular events in living cells or tissue in near real time would also represent a substantial advance in the art. What is therefore described is a device and analytical platform for the evaluation of samples with volumes consistent with the contents of a single cell or smaller that provides for near real-time analysis, increased throughput and reduced costs.

The present invention includes an apparatus for analyzing a sample comprising a probe having a plurality of domains disposed thereon, wherein the domains form an array. Suitably, the array is a nanoarray. The domains suitably comprise biomolecules selected from the group consisting of drugs, chemical groups, lipids, DNA, RNA, proteins, peptide species, carbohydrates, and any combination of these entities. Optionally, nanosensors are operably connected to one or more of the domains.

The probe suitably comprises a microcantilever. In some embodiments, the probe is a dual element probe or a multielement probe. Some embodiments of a probe of the invention comprise at least one microdisrupter disposed on the probe. Optionally, at least one microdisrupter comprises a tip or pointed member. The invention also encompasses probes comprising at least one hydrophobic region. Also described are embodiments wherein a suitable molecular detection device is operably connected to the probe. Suitable molecular detection devices include scanning tunneling microscopes, atomic force microscopes, mass spectrometers, fluorescence microscopes, flow cytometers, Raman spectrometers, Infra-red spectrometers, UV spectrometers, electronic systems, electrochemical systems, optical systems, magnetic and electromagnetic systems, and mass measuring systems.

Another aspect of the invention includes a method of detecting a molecular interaction event comprising contacting a sample with a probe having a plurality of domains disposed in an array, providing an incubation period, washing unbound molecules from the domains and detecting the molecular interaction event. Suitably, the sample comprises at least one cell or at least one cell lysate.

Also described is a method of detecting one or more molecules in a sample comprising contacting the sample with a probe having a plurality of domains disposed thereon, wherein the domains form an array, and wherein the domains are operably connected to one or more sensors, including nanosensors; and detecting binding of one or more molecules to one or more of the domains.

The present invention also provides a method of analyzing one or more analytes in a cell comprising disrupting a cell with a microdisrupter disposed on a probe, wherein the probe has a plurality of domains disposed thereon, and wherein the domains form a nanoarray; passing the nanoarray through the membrane of the cell such that the nanoarray contacts intracellular space; and detecting the binding of one or more analytes to the nanoarray. Suitably, the method further comprises passing the probe through the nuclear membrane such that the nanoarray contacts the intranuclear space. Alternatively, the method can comprise inserting the probe into a cellular organelle. Cellular organelles suitable for analysis are those selected from the group consisting of a golgi complex, a mitochondria, a lysosome, an endoplasmic reticulum, a lipid raft, a cytoskeletal system, and any other physically or chemically definable cellular or sub-cellular domain or system.

The invention also encompasses a method of retrieving at least one analyte from a sample comprising contacting the sample with a probe having a plurality of domains disposed thereon, wherein the domains form an array; and retrieving at least one analyte from the molecular domains.

Also provided is a method of delivering at least one substance to a cell comprising reversibly attaching at least one substance to a probe having a plurality of domains disposed thereon, wherein the domains form an array; passing the probe through the membrane of the cell into the intracellular space; and releasing at least one substance into the intracellular space. Suitably, reversibly attaching at least one substance to a probe comprises contacting the substance to the domains such that a binding event occurs. Suitable substances include drugs, chemical groups, lipids, DNA, RNA, proteins, peptide species, carbohydrates and any combination of these entities. A suitable means of reversibly attaching comprises tethering at least one substance to at least one domain with a protease substrate. Additional methods include, but are not limited to, photolytic tethers, temperature sensitive tethers, ionically sensitive tethers, and chemically sensitive tethers.

BRIEF DESCRIPTION OF THE FIGURES

FIG. 4 depicts experimental data showing protein arrays created on microfabricated atomic force microscope probe cantilevers. The arrays are rendered fluorescent by reaction with a fluorophore-coupled antibody that is specific for the deposited protein. The inset is a brightfield image showing the deposited protein domains prior to fluorescent labeling.

FIG. 5 depicts brightfield micrographs of a variety of microfabricated probes.

FIG. 6 depicts a brightfield micrograph of a two-component (two protein) array deposited on a probe of the type shown in FIG. 5.

DETAILED DESCRIPTION OF THE PREFERRED EMBODIMENTS

The interrogation of extremely small sample volumes can be accomplished with the present invention. Provided are apparatuses including probes for analyzing a sample with an array. Suitable methods for using the probes of the invention are also provided.

Probes

As used herein, a "probe" refers to any suitable mechanical structure upon which an array can be composed and which can be used to interrogate a sample of small volume. Suitable probes include microfabricated structures. "Microfabricated structures" are millimeter, sub-millimeter or sub-micron scale structures and are generated by techniques known in the art including, but not limited to, laser ablation, electrodeposition, physical and chemical vapor deposition, photolithography, wet chemical and dry etching, injection molding, electron beam lithography, and X-ray lithography. Other suitable probe structures for use in the present invention include biological microstructures such as eyelashes, cochlear hair cells, flagellum and actin filaments. Microcantilevers are also considered to be suitable for use as probes in the present invention and can include any of the above-described structures anchored at one or more ends or surfaces. Any portion of the cantilever can be used as a suitable anchor point. In some cases there may be multiple anchor points.

Figure 1:
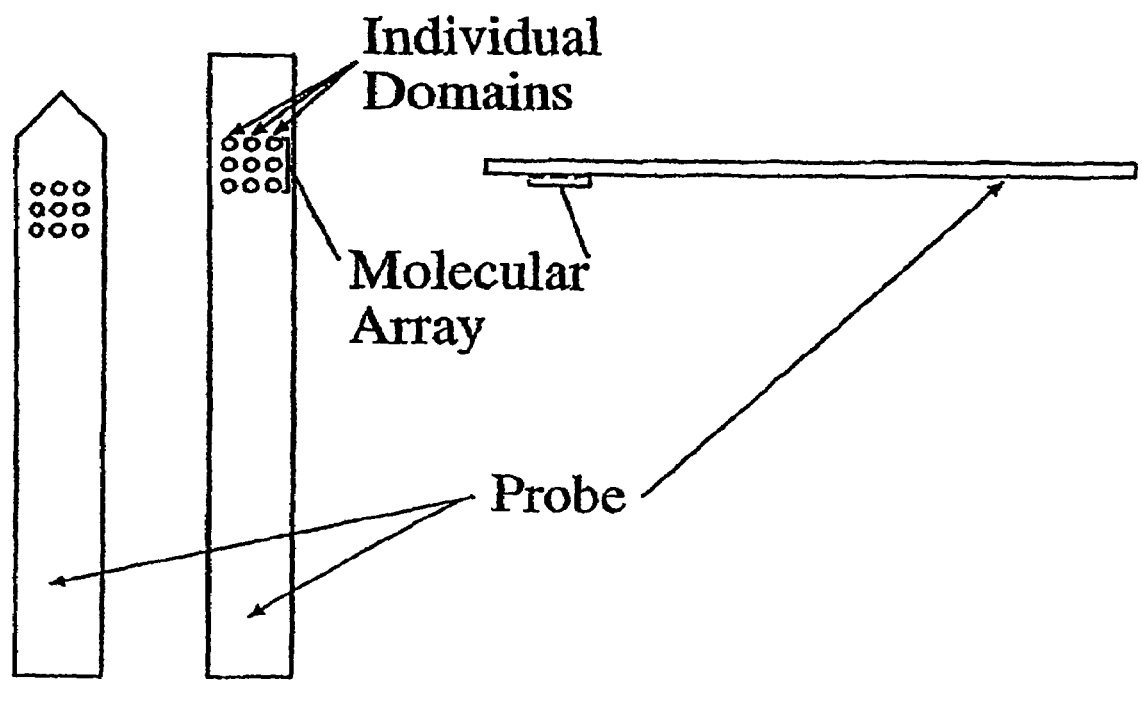
FIG. 1 is a schematic view of several embodiments of the invention showing mechanical micro4disrupter features.
Figure 1:
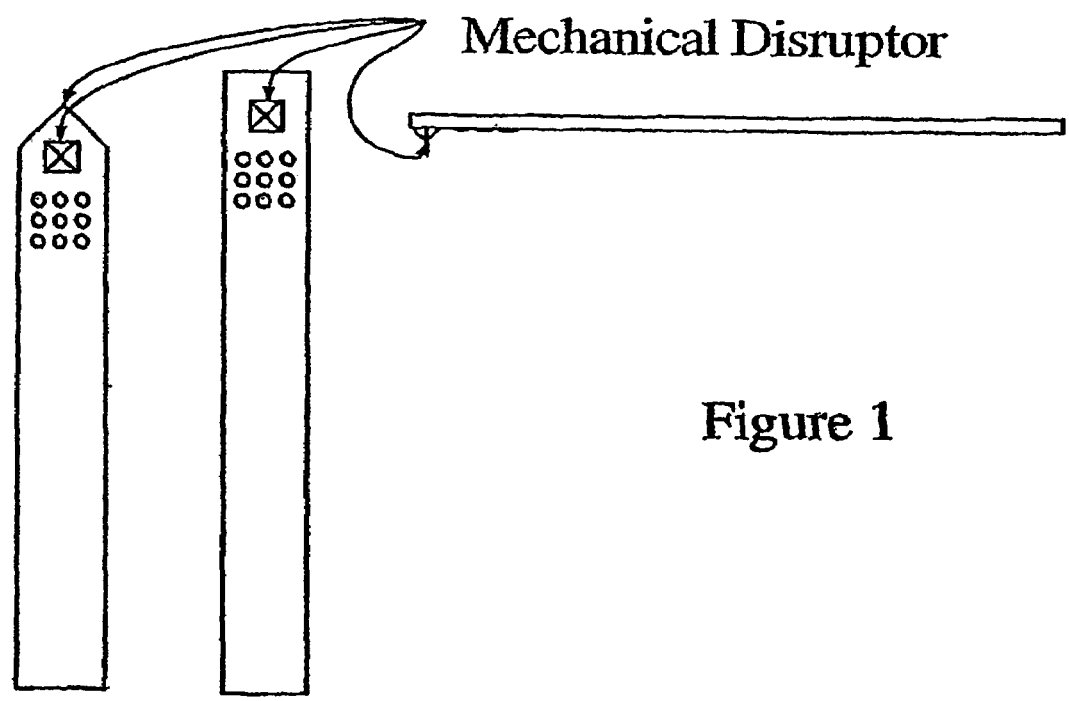

Optionally, a probe of the invention may include "microdisrupters," which, as used herein, are features that are suitable for disrupting a cell. Two mechanical embodiments of the microdisrupter feature are exemplified and depicted in FIG. 1. "Disruption" of a cell includes any suitable technique by which the interior of a cell is accessed. "Disrupting" includes, but is not limited to, puncturing, penetrating, perturbing, oscillating, sonicating and lysing. Structures or features suitable for use as microdisrupters include tips or pointed members, serrated edges, pores, annulas, spheres or spherical members, enzymes such as lipases or proteases capable of digesting all or a part of a cell membrane, hypotonic or hypertonic compositions capable of altering the osmotic pressure of a cell and thermal or electromagnetic energy delivery devices including, but not limited to, photodiodes, lasers, electrical sources, temperature sources and radiowave sources. It should be noted that a probe having no additional microdisrupter disposed thereon may itself be used to access the interior of a cell through micromanipulation or the delivery of energy, enzymes or compositions as described above.

Probes of the invention are not limited to single element structures. For example, dual or multi-pronged probes are included within the scope of the invention. Each element, or "tine," of a multi-pronged probe can include an array. Arrays on adjacent prongs can be identical or can be different, having domains of different species, or even different types of molecules. For example, one prong can have an array of DNA species and an adjacent prong can have an array of peptide species. Some prongs may not have an array disposed thereon. Additional prongs, if present, may serve the further function of disruption as described above, and may also include microdisrupters disposed thereon.

Probes of the invention may include anti-wicking features to prevent capillary action from drawing the sample away from the array. Suitable features include hydrophobic domains and mechanical structures that are physical barriers to wicking. Hydrophobic domains may be disposed on the surface of the probe or may be an integral component of the probe. Hydrophobic domains may comprise any portion of the probe, but are suitably constructed so as to facilitate maintained contact between the sample and the array. In this regard, hydrophobic domains may be used in conjunction with hydrophilic domains, which are most suitably disposed adjacent to, or as a substrate for, the array. Mechanical structures that are suitable for use in preventing wicking include O-ring structures, micro-dikes, micro-walls, bumps, protrusions, holes, cavities, filters and temperature gradients.

Arrays

As used herein an "array" refers to a plurality of spatially arranged domains disposed in known locations, or "addresses" on a probe of the invention. A "nanoarray" is an array in which each domain has a total area of about 100 $\mu^2$ (a diameter of about 5.6 $\mu$ for round domains, or a side dimension of about 10 $\mu$ for square domains), and preferably a total area of less than about one micron. A "domain" or a "molecular domain" or an "affinity domain" is a discrete region of immobilized species including, but not limited to, chemical species, biomolecular species such as nucleic acids and peptides, and molecular and sub-molecular species. Specific non-limiting examples include antibodies, DNA, RNA, normally or abnormally expressed cellular proteins, pathogens and antigens derived therefrom, reactive organic and inorganic chemical groups and multi-component complexes. It should be noted that as used herein, "peptide species" can include single amino acids, peptides, polypeptides and/or proteins.

Domains may further include nanosensors coupled to the immobilized species. "Nanosensor," as the term is used herein, refers to any reporter system that enables direct detection of interaction events or molecular activities occurring on the micron or smaller scale. The construction of suitable nanosensors for use in the present invention are described in copending application Ser. No. 09/974,755, entitled "Nanoscale Sensor" which is incorporated herein by reference in its entirety. Briefly, nanosensors provide for the monitoring of nanoscale events by the detection of measurable changes in physical position, mass, electrical capacitance, conductivity or resistance, resonance frequency, resonance amplitude, morphology, kinetic energy, local temperature, oxidation/reduction (redox) state, structural integrity, bonding energy or other properties of the array species. Suitable structures for use as nanoscale sensors include carbon nanotubes, fullerene structures, nanobars and nanowires.

Arrays can be constructed on probes by any suitable methodology. One technique used in the construction of ultraminiturized arrays suitable for use in the present invention is described in copending application Ser. No. 09/929, 865, entitled "Nanoscale Molecular Arrayer," incorporated herein by reference in its entirety. This technique operates via piezoelectric, mechanical, magnetic or other methods for manipulation of a probe to deposit and reproduce domains smaller than about 1 micrometer to as little as ten nanometers or less. Briefly, a suitable method for constructing arrays includes loading deposition materials on a deposition probe and transferring the materials to a deposition substrate using an apparatus having X, Y and Z controllers for manipulation of the probe, a humidity controller, and a control computer. Additional optional components of an apparatus suitable for constructing arrays include a force feedback monitor and an optical microscope.

The ultraminiaturized attributes of some probes of the invention allow the construction of arrays with dimensions on the scale of a few microns and with molecular arrays formed from at least 2 to about 250 molecular domains of smaller than 1 micrometer down to as little as 10 nanometers or less each.

Molecular Detection Devices

As used herein, "molecular detection devices" include devices suitable for reporting microscopic or submicroscopic events on a macroscopic scale. The ability to measure events that occur on minute scales and report these events in the macroscopic world is of clear utility. One device suitable for the direct detection of molecular interaction events occurring at the micro- or nano-scale level is the scanning probe microscope. One type of scanning probe microscope is the atomic force microscope ("AFM"). In atomic force microscopy, the interactions between a sharp, micron-scale probe and a sample are monitored and regulated as the probe raster scans over the sample. Extremely fine control of the motion of the AFM probe is achieved using piezoelectric crystals. The AFM is capable of about two nanometer (or less) lateral resolution and less than one Angstrom vertical resolution. It can be operated in a vacuum, in atmospheres of varying humidity or in physiological solution, and is capable of identifying and measuring molecular binding events in near-real time. The resolution of the AFM can be very high, even on the atomic scale in some cases.

In addition to its high spatial resolution, the AFM is capable of exerting and detecting forces in the picoNewton (pN) range. This is the force range relevant to the forces extant between and within molecules. Thus, the AFM can measure intermolecular, as well as intramolecular bonding, or "rupture," forces. This is accomplished by repeated cycling of the AFM probe through an approach/retract sequence. Moreover, the AFM can measure a wide variety of other forces and phenomena, such as magnetic fields, thermal gradients and viscoelasticity.

Ultraminiaturization of molecular arrays is the next step in the evolution of microarray methodologies. Through ultraminiaturization, vast increases in throughput can be achieved, along with reductions in costs. Moreover, ultraminiaturization allows for the utilization of such small sample volumes that the methods necessary for recovery of sample materials can be virtually non-invasive, thereby greatly enhancing the comfort level of the sample donor. For example, rather than a painful tissue biopsy, a few cells obtained by a simple swab technique can provide the same level of information. Ultraminiaturization of arrays would allow for in situ, and even in vivo, detection of molecular and biomolecular events in real time, without the need for sample retrieval. Nonetheless, to date, no viable methodologies or devices for accomplishing these goals have been described.

Microscopic or submicroscopic events include intermolecular and intramolecular interaction events. One measurable intramolecular event is known as a "rupture event," and is defined herein as the force necessary to induce the breaking of intramolecular bonds. Other typical events that are suitably measured and reported by molecular detection devices include the binding of one molecular species to another molecular species via covalent, non-covalent, hydrophobic, electrostatic or hydrogen bonding, or a combination of these or other bonding mechanisms. Non-limiting examples useful in the investigation of disease and therapeutic strategies include antibody-antigen interactions, receptor-ligand interactions and enzyme-substrate interactions.

Methods of molecular detection suitable for use in the present invention include inverse cyclic voltametry and other methods using electronic platforms, including but not limited to piezoelectric, capacitance, electromagnetic and laser-based devices. Other methods include the use of chemical reactions, changes in mass, bonding force, redox state, structural integrity, fluorescence, absorbance, quenching, local structural variation, kinetic energy, thermal energy, magnetic or electromagnetic reactivity, radio energy generation or absorption, general energy state and radioactivity to report binding events.

As discussed, the atomic force microscope is one instrument that is particularly useful in practicing an embodiment of the present invention. Other suitable instruments include scanning tunneling microscopes, mass spectrometers, fluorescence microscopes, flow cytometers, Raman spectrometers, Infra-red spectrometers, UV spectrometers, electronic systems, electrochemical systems, optical systems, magnetic and electromagnetic systems, and mass measuring systems. As discussed above, nanosensors can also be used to report molecular events. Coupling nanosensors to an electronic measuring device including, but not limited to an amp meter, conductivity meter, ohm-meter, or oscilloscope allows for the macroscopic detection of binding and other molecular events.

Molecular detection devices can be operably connected to probes of the invention. As used herein, "operably connected" refers to electric, magnetic, mechanical, optical, pneumatic or other means of connecting the probe and the molecular detection device such that the macroscopic reporting of the molecular interaction event can be made simultaneously or in near-real time.

Methods

Probes of the invention may be used in situ or ex situ. As used herein, "in situ" usage refers to direct detection or measurement of molecular or sub-molecular events upon introduction of the array at the site of interest. For example, in situ usage includes in vivo interrogation of a sample with a probe. In contrast, "ex situ" usage refers to removing the sample from the site of interest prior to interrogation with the probe.

Figure 3:
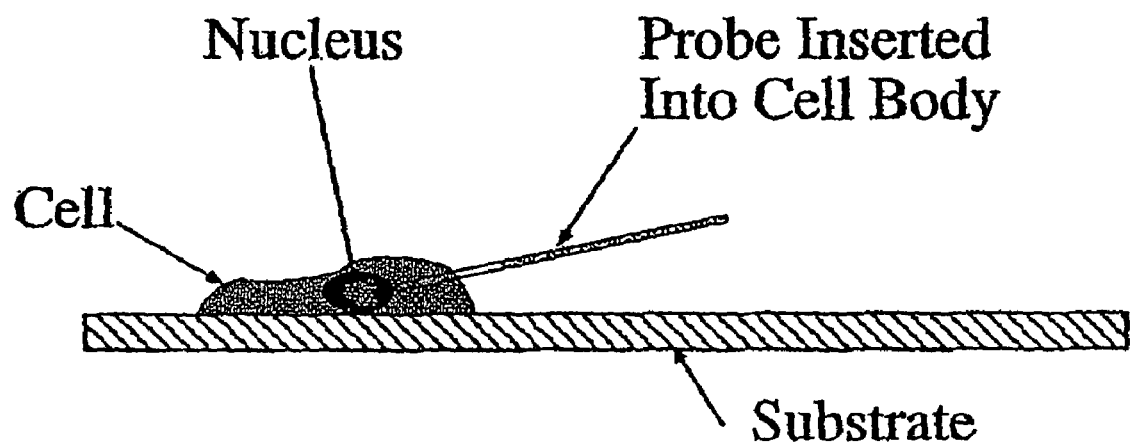
FIG. 3 depicts the use of the invention for direct interrogation of intracellular contents.

A probe of the invention can be used to directly interrogate a single living or non-living cell, as shown in FIG. 3. Methods of isolating single living cells are known in the art. For example, U.S. Pat. No. 6,420,105, incorporated herein by reference, describes a method of isolating and harvesting a single cell from its organ tissue using a device capable of collecting cells so that they remain substantially intact. Positioning and motion of the probe is accomplished using piezoelectric or similar motion control devices. In some embodiments, it is possible to specifically target subcellular domains such as the nucleus, or a specific organelle, such as a Golgi body. Suitably, a probe having a pointed member or other microdisrupter device situated thereon is inserted directly into a cell or positioned adjacent to the cell. Alternatively, a probe without a microdisrupter device can enter a cell or the cell can be lysed by any suitable means prior to interrogation. The components of the cellular environment are then allowed to interact with the molecular array on the probe.

In some cases, the amount of applied vertical force exerted by the probe on the sample is regulated by monitoring the degree of flexion of the probe using such methods including but not limited to strain gauges, optical lever systems, integrated piezo resistive methods, or other suitable methods. Motion of the probe can be in the X, Y plane and in the Z plane. In addition, ultrasonic energy can be imparted by rapid oscillations of the probe. These motions are accomplished using piezo ceramic motion control mechanisms, mechanical methods or other methods that are known to skilled practitioners in the art.

Figure 2:
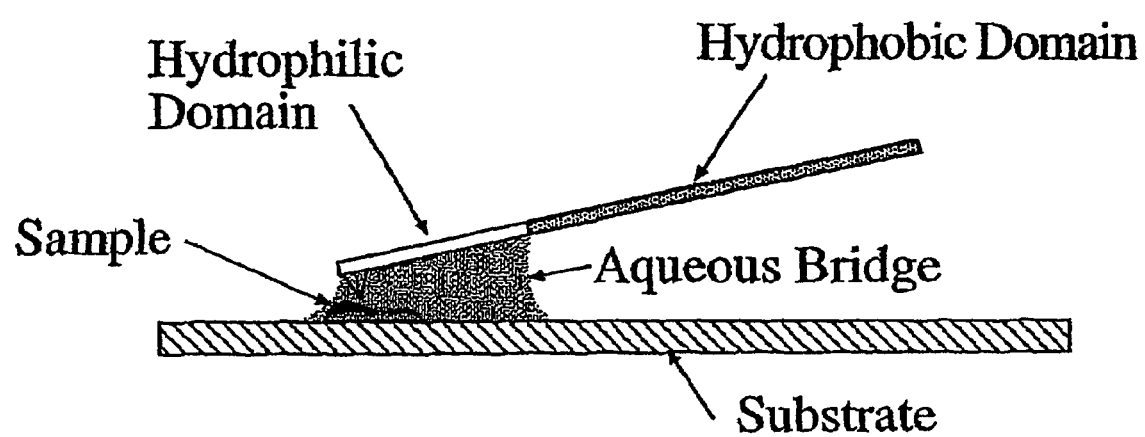
FIG. 2 depicts use of an aqueous bridge with a probe of the invention having a microdisrupter and hydrophilic and hydrophobic domains.

The array can contact the sample by any suitable direct or indirect means. An example of an indirect means of contacting a sample includes the use of an aqueous bridge, as shown and depicted in FIG. 2. Hydrophilic and hydrophobic domains on the probe can be advantageously used to maintain contact between the sample and the array. When an aqueous bridge is used, a small drop of fluid deposited on the sample cell is captured between the probe and the cell and supporting substrate as shown in FIG. 2. The sample is mechanically disrupted by motion of the probe and contact with the microdisrupter. As the sample is disrupted, the materials released diffuse through the aqueous bridge and contact the molecular domains on the probe. Specific capture agents on the array bind to components of interest contained in the sample. As discussed above, binding events are monitored by a variety of methods including, but not limited to, atomic force microscopy, fluorescence, Raman and IR scattering, mass spectrometry, electronic signatures, or changes in mechanical or resonance properties of the probe itself.

Biomarkers are one type of suitable target molecule for probes of the invention. As used herein, a "biomarker" is any molecule that can be used as an identifier of a particular cell, cell type, cell state, physiological state of an organ, organ system, or whole organism, tissue, tissue type, tissue state, predisposition to disease including but not limited to cancer, drug tolerance, cytotoxicity effects and mental or psychological function. Typically, biomarkers are proteins, but can also be cell-surface peptides, intracellular peptides, lipids, carbohydrate moieties, RNA transcripts and/or DNA molecules, chemical groups, and/or circulating antigens.

Another suitable target for molecular analysis using methods of the invention is body fluid. A "body fluid" may be any liquid substance extracted, excreted, or secreted from an organism or tissue of an organism. Body fluid may or may not contain cells. Body fluids of relevance to the present invention include, but are not limited to, whole blood, plasma, serum, urine, cerebral spinal fluid, tears, sinovial fluid, semen, mucus and amniotic fluid.

Probes of the invention can also be used to retrieve an analyte from a complex solution. As used herein, an "analyte" refers to any substance, molecule of interest, biomolecule of interest, or particle for which information is desired. In this aspect, the arrays of the invention suitably comprise molecular domains capable of reversibly binding the analyte either for direct measurement on the probe, or for release and subsequent measurement by further analytical techniques. As will be appreciated by those of skill in the art, this embodiment can also be used to concentrate an analyte in a complex solution.

A further embodiment of the present invention is a method of delivering one or more substances to a living or non-living cell, tissue, or organism. In this embodiment, the domains of an array are "loaded" with the substance or substances to be delivered, which is suitably attached to the molecular domains by, for example, a protease labile tethering molecule. Suitable protease labile tethering molecules comprise a peptide sequence that is susceptible to being hydrolyzed by one or more proteases found in the target cell, tissue or organism. Some non-limiting examples of protease labile tethering molecules include short-chain peptide substrates of serine proteases, metalloproteases, aspartate proteases and cysteine proteases. Additional tethering molecules include, but are not limited to, ion sensitive tethers (e.g., leucine zippers, chelaters (EDTA)), temperature sensitive tethers (e.g., PNA, DNA or RNA), photosensitive tethers, or chemically sensitive tethers. Substances that are suitable for delivery by probes of the invention include genes, polynucleotides comprising coding sequences, enzymes involved in DNA replication, transcription or translation, enzymes involved in cellular metabolism or other processes, restriction endonucleases, ligases, reactive species such as free radicals, drug candidates and drugs. As will be appreciated, the molecular domains of a probe can be loaded for delivery of multiple molecules of the same substance or different substances, which may or may not act in concert. For example, a gene of interest can be delivered to a living cell simultaneously with enzymes that can be used to splice it into the appropriate site of the host DNA.

Additional details of the invention will become more apparent by reference to the following non-limiting examples.

EXAMPLES

Printing Proteins on Microcantilevers

Protein arrays with approximately 1 μm diameter spot sizes have been printed on microcantilevers using the method described herein. FIG. 4 shows two examples of AFM cantilever onto which rabbit immunoglobulin G (IgG) has been printed. The IgG was placed in the pattern shown using a nanoscale molecular arrayer (hereinafter, "NanoArrayer") as described in copending application Ser. No. 09/929,865. Once printed, the IgG was visualized by forming a complex with a second antibody, anti-rabbit IgG antibody conjugated to the fluorescent reporter molecule Alexa-594 and observed in a fluorescence microscope using the appropriate wavelength filters.

Gold-coated AFM cantilevers (dual leg design with various spring constants) were placed in the NanoArrayer. A deposition tool (a microfabricated device for lacing molecules on surfaces) was front-loaded by immersion in a solution of the rabbit IgG containing 1 mg/ml antibody in a solution lacking any non-volatile salt but containing glycerol and non-ionic detergent in distilled water. The deposition tool was removed from the loading solution and brought into contact with the gold coated AFM probe under careful control of local humidity and temperature (typical humidity >50% RH at RT) and the deposition process accomplished by physical transfer of materials from the deposition tool to the gold surface. This process was repeated until the pattern shown in the figure was achieved. The gold-coated microcantilever was then incubated in a blocking solution containing Tris-HCl, pH 7.2, 100 mM casein for 30 minutes and rinsed briefly with distilled water. The secondary antibody was then added in a buffered solution containing Tris-HCl, pH 7.2, 50 mM NaCl and incubated for 30 minutes at room temperature. The cantilever was again briefly rinsed with distilled water and viewed in a fluorescence microscope. The presence of fluorescence in discrete domains demonstrates that the rabbit IgG was printed on the microcantilever as expected. This experiment demonstrated that it is feasible to practice the invention and print biomolecular patterns on microfabricated devices that are the same size scale as a single cell.

Printing Proteins on Microfabricated Devices

In another embodiment, a protein pattern was printed on a specially constructed microcantilever device ("probe"). The probe contained a sharp point as the mechanical disrupter disclosed in this application. Examples of probes are shown in FIG. 5.

Solutions of rabbit and mouse IgG (Jackson ImmunoResearch, PA) were diluted to 1 mg/ml in phosphate buffered saline, pH 7.4 (PBS). These solutions were mixed 1:1 with spotting buffer containing non-ionic detergent, glycerol but no non-volatile salt, and approximately 0.5 µl of each was deposited onto a glass coverslip by hand pipetting and placed on the NanoArrayer printing stage. These solutions then served as the loading domains to front-load microfabricated depositions tools in the NanoArrayer. The deposition tool was treated with UV light (254 nm) for 30 minutes to enhance the loading process by increasing the hydrophilicity of the tool. The deposition tool was loaded by immersion of its distal end in a spot of sample solution. The probe onto which an array of antibodies were to be printed was immobilized on the NanoArrayer printing stage using double-stick tape. Arrays of the first antibody solution were printed using time-controlled mechanical contact between the deposition tool and the surface of the probe. The deposition tool was washed in distilled water in between sample loads to ensure no cross-contamination of spotted antibodies. The deposition tool was then reloaded with a second antibody and used to deposit a second array, adjacent to the first, on the probe. The results of this process are shown in FIG. 6, depicting two 3-spot arrays created on a single probe using this method. Arraying was performed at room temperature with 55% relative humidity.

Post-Deposition Processing

Following printing the probe is incubated for 3 hours in the NanoArrayer environmental chamber at a relative humidity of 70% to allow complete binding of the deposited antibodies onto the probe surface. After humidification the surface was be blocked by immersion in 100 mM casein (in distilled water) for 30 minutes at room temperature, followed by 3 washes in PBS containing 0.2% Tween-20 (PBST).

Optical-Detection and Data Collection

Antibody spot morphology was assessed by tagging the deposited antibodies with Alexa-594 anti-mouse and Alexa-488 anti-rabbit antibodies (Molecular Probes). The arrays of antibodies on the probe were read on a standard fluorescence microscope (Nikon TE-2000 inverted microscope and with a Hamamatsu ORCA-ER 1.3 megapixel cooled CCD camera). Data from an entire nanoarray experiment was captured in a single image using a 40× or 60× objective. Data was analyzed using Media Cybernetics Array-Pro v. 4.5 software that was specifically developed for microarray analysis and is suitable for nanoarray analysis as well.

Surface Chemistry for Tethering Biomolecules

For successful deposition of antibodies or other biomaterials on probes, the surface chemistry must supply uniform monolayer immobilization, maintenance of native antibody state with accessibility to molecular targets in the sample, array stability, and negligible background binding. In the development of standard nanoarrays, multiple surface chemistries have been tested. One non-limiting chemistry approach for deposition onto the probes described in the above examples is an amine reactive self-assembled monolayer (SAM) on a gold coated probe. The SAM consisted of a succinimide-terminated alkanethiolate that was specific for primary amines on the molecule to be tethered. These surfaces exhibit high protein binding while active, but are easily deactivated by humidification to yield a surface with very low non-specific binding characteristics.

The probe was cleaned in water and ethanol, followed by treatment for 45 minutes with UV and ozone (broad wavelength Hg-vapor bulb that creates local ozone via reaction with oxygen). The probes were coated with 5 nm chromium followed by 10 nm of gold in an ion beam sputter. Immediately following sputtering, probes were immersed in a 0.5 mM solution of DSU (dithiobis-succinimidyl undecanoate, DSU; Dojindo Molecular Technologies, Inc., MD) dissolved in 1,4 dioxane, and incubated for 3 hours at room temperature, Probes were washed and briefly sonicated in 1,4 dioxane, blown dry, and stored at room temperature under dry $N_2$ gas.

A related approach is to use a compound having an alkanethiolate with a polyethylene glycol spacer and an epoxide terminal group. The alkanethiolate will form a tight monolayer on gold, the PEG spacer will resist non-specific protein adsorption while allowing rotational freedom for capture molecules, and the promiscuous epoxide functional group will react with primary amines on the deposited proteins. Unreacted epoxides will hydrolyze in the presence of water to yield a diol that should have excellent non-specific adsorption properties. The increased rotational freedom of captured molecules that will be realized on this surface may positively impact access of the sample molecules by detection antibodies and will therefore be tested for reverse-phase applications.

Additional methods for tethering proteins and other biomolecules include, but are not limited to, spontaneous adsorption, hydrophobicity mediated adsorption, covalent coupling sulfur-gold binding, use of a polyethylene glycol spacer with various distal chemistries, silane mediated covalent coupling, ionic binding, electrostatic binding and biomolecular binding to pre-existing molecular layers including protein-protein, protein-nucleic acid, receptor-ligand and nucleic acid-nucleic acid interactions.

The following prophetic examples describe uses of the devices created using the invention.

Prenatal and Neonatal Screening

A small amount of prenatal (e.g., amniotic) or neonatal material is obtained. This material may be a blood sample, serum sample, body fluid, cell sample or any other biological sample for which a genetic or biomarker screen is desired. In the case of blood, a microdrop of the material is prepared by pipetting onto a glass slide that is maintained in a humid environment to prevent evaporation. A nanoarray probe is brought into close proximity to the microdrop and inserted into the drop to allow the biomaterials on the drop to contact the molecular domains on the chip on a tip. After a suitable incubation period, the probe is removed from the microdrop, and the array is washed and analyzed by fluorescence, atomic force microscopy, or other methods known to those practicing the art.

In an alternative embodiment of this example, a small number of cells are obtained from a subject and maintained in a living state on a suitable substrate such as a glass slide or silicon chip. A nanoarray probe is carefully introduced into a cell through the cell membrane and allowed to interact with materials within the cell's cytoplasm, nucleoplasm or other sub-cellular location. After a suitable incubation period, the probe is removed from the cell, rinsed and evaluated as described above.

Forensics

Typical forensic samples include cellular materials, body fluids and trace chemicals. In one application of the present invention, a blood sample is recovered from a crime scene. There is insufficient material to complete a protein-based biomarker screen or a DNA fingerprint analysis without amplification. In one embodiment, a protein biomarker array on a probe of the invention is brought into proximity with the sample which has been resuspended in a minimal volume (less than one microliter) to maintain the highest concentration possible of low copy number protein biomarkers. After a suitable incubation period, the probe is processed as described above and a protein biomarker profile is obtained and can be used as a "signature" to identify or rule out a suspect.

Minimally Invasive Cancer Diagnostics

In many cases, the acquisition of necessary biopsy material for a diagnostic cancer screen is a very painful process for the patient. This is largely due to the relatively large amount of biopsy material necessary for adequate testing. Use of an ultraminiturized array on a microprobe greatly decreases the amount of required material for a diagnostic screen, opening the door to methodologies that enhance patient comfort considerably. For example, rather than a major surgical procedure to obtain a suspect breast tumor, a relatively small needle is inserted into a tumor with minimal discomfort, and a small number of suspect cells is withdrawn. A cancer biomarker specific probe is juxtaposed to the cells and either the insertion or disruption technique is used to analyze the cellular content for cancer specific biomarkers.

It is envisioned that certain tissue suspected of being malignant (e.g., throat tumors) could be sampled by swabbing to obtain a few cells that could be interrogated and analyzed as described above.

Delivery and Release of Biomaterials into Cells

In this example, rather using the probe to recover materials, a reverse procedure is carried out. A probe is "loaded" with a variety of materials, for example, DNA splicing enzymes, that are bound to specific sites on the array. The probe is then inserted into a specific cell or group of cells. By using a protease labile tether method, the biomaterials are released within the cells and allowed to carry out their bioactivity in a very cell specific fashion. This multiplexed delivery of materials to specific cells provides for the retention of materials in an unreacted, "dormant" state on the probe until they are inserted into the cells and allowed to mix. This is particularly applicable in situations calling for site-specific modification of cells is desirable, such as in gene therapy embodiments.

Transgenic Analysis

In this example, the goal is to evaluate small numbers of cells for their ability to grow into healthy transgenic animals. It is known that at early divisional stages of embryogenesis, it is possible to remove single cells without disrupting the growth of the embryo, assuming the embryo is otherwise normal and healthy. However, embryos that are morphologically normal can carry aberrant genes or metabolic anomalies that will result in unhealthy or dead newborns. To avoid this, it is desirable to carry out a biomarker profile of the embryo at an early stage. In this scenario, the probe is diagnostic for a group of biomarkers that are indicative of normal cellular growth and function. A single cell is removed from the embryo at an early stage. The probe is inserted into or used to disrupt the cell and the cell contents allowed to interact with the affinity domains on the probe. The probe is subsequently processed and the biomarker screen used to make a determination as to the health and utility of the embryo long before the expense and technical difficulty of carrying a defective transgenic animal to term are encountered.

Complex Biopsy Screening

A popular method for isolating different cell types from complex tissues is known as Laser Cell Microdissection ("LCM"). In this method, a laser is used to cause adherence of specific cells to an adhesive backing which is then removed with the cells intact. These cells can be processed by conventional PCR methods to amplify DNA content, but the cell number is typically far too low to enable processing of protein profiles. A probe of the invention carrying the desired protein profiling affinity agents on the array can be used, either by insertion or disruption, to analyze the protein content of these dissected cells.

It should be noted that, as used in this specification and the appended claims, the singular forms "a," "an," "the" include plural referents unless the content clearly dictates otherwise. Thus, for example, reference to a method of detecting "a biological event" includes a method of detecting multiple biological events. It should also be noted that the term "or" is generally employed in its sense including "and/or" unless the content clearly dictates otherwise.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

We claim:

1. An apparatus for analyzing a sample comprising a probe, the probe comprising a pointed member, the pointed member having a plurality of domains disposed thereon, wherein the domains comprise one or more biomolecules and wherein the domains form an array.

2. The apparatus of claim 1, wherein the array is a nanoarray.

3. The apparatus of claim 1, wherein the one or more biomolecules are selected from the group consisting of drugs, drug candidates, chemical groups, lipids, DNA, RNA, proteins, peptide species, carbohydrates, and any combination thereof.

4. The apparatus of claim 1, further comprising nanosensors operably connected to one or more of the domains.

5. The apparatus of claim 1, wherein the probe is a dual element probe.

6. The apparatus of claim 1, wherein the probe is a multielement probe.

7. The apparatus of claim 1, wherein the probe is sized to interrogate a sample comprising a volume of about 50 femtoliters to about 10 microliters.

8. The apparatus of claim 1, the apparatus comprising at least one microdisrupter disposed on the probe.

9. The apparatus of claim 8, wherein the microdisrupter comprises the pointed member.

10. The apparatus of claim 1, wherein the probe further comprises at least one hydrophobic region.

11. The apparatus of claim 1, further comprising a molecular detection device operably connected to the probe.

12. The apparatus of claim 11, wherein the molecular detection device is a scanning tunneling microscope, atomic force microscope, mass spectrometer, fluorescence microscope, flow cytometer, Raman spectrometer, Infra-red spectrometer, UV spectrometer, electronic system, electrochemical system, optical system, magnetic and electromagnetic system, or mass measuring system.

13. A method of detecting a molecular interaction event comprising:
   contacting a sample with the probe of claim 1;
   providing an incubation period;
   washing unbound molecules from the domains; and
   detecting the molecular interaction event.

14. The method of claim 13 wherein the sample comprises at least one cell.

15. The method of claim 13 wherein the sample comprises at least one cell lysate.

16. A method of detecting one or more molecules in a sample comprising:
   contacting the sample with the probe of claim 4; and
   detecting binding of one or more molecules to one or more of the domains.

17. The apparatus of claim 1, wherein the domains are spatially arranged in known locations.

18. The apparatus of claim 1, wherein the probe is sized to interrogate a single cell.

19. The apparatus of claim 1, wherein the probe is sized to interrogate a lysate of a single cell.

20. The apparatus of claim 1, wherein the probe is sized to interrogate a sub-cellular species of a cell.

21. The apparatus of claim 20, wherein the sub-cellular species is selected from the group consisting of a Golgi complex, a mitochondria, a lysosome, an endoplasmic reticulum, a lipid raft, and a cytoskeletal system.

22. The apparatus of claim 1, wherein the pointed member is sized to be inserted into a cell.

23. The apparatus of claim 1, wherein the pointed member comprises an anti-wicking feature.

24. The apparatus of claim 23, wherein the anti-wicking feature comprises a hydrophobic domain.

25. The apparatus of claim 1, wherein at least one domain has a substance reversibly attached thereto.

26. The apparatus of claim 25, wherein the at least one domain is reversibly attached by a tether, the tether comprising a protease substrate, a photolyzable tether, a chemically reactive tether, an ionically reactive tether, or a thermally sensitive tether.

27. A method of delivering at least one substance to a cell, comprising:
   passing the pointed member of the probe of claim 25 through the membrane of the cell into the intracellular space; and
   releasing the substance into the intracellular space.

28. A method of analyzing one or more analytes in a cell, comprising:
   passing the pointed member of the probe of claim 1 through the membrane of the cell into the intracellular space; and
   detecting the binding of the analyte to the domains of the array.

29. The method of claim 28, wherein the array is a nanoarray.

30. A method of retrieving an analyte from a cell, comprising:
   passing the pointed member of the probe of claim 1 through the membrane of the cell into the intracellular space, wherein the probe has at least one domain capable of binding to the analyte; and
   retrieving the analyte from the domain.

31. A method of detecting an in situ molecular interaction event comprising:
   contacting a sample with the pointed member of the probe of claim 1; and
   detecting the molecular interaction event.

32. The apparatus of claim 3 wherein the one or more biomolecule is a drug.

33. The apparatus of claim 3 wherein the one or more biomolecule is a drug candidate.

34. The apparatus of claim 3 wherein the one or more biomolecule is a chemical group.

35. The apparatus of claim 3 wherein the one or more biomolecule is a lipid.

36. The apparatus of claim 3 wherein the one or more biomolecule is DNA.

37. The apparatus of claim 3 wherein the one or more biomolecule is RNA.

38. The apparatus of claim 3 wherein the one or more biomolecule is a protein.

39. The apparatus of claim 3 wherein the one or more biomolecule is a peptide species.

40. The apparatus of claim 3 wherein the one or more biomolecule is a carbohydrate.

41. An apparatus for analyzing a sample comprising a probe, the probe comprising a pointed member, the pointed member having a plurality of domains disposed thereon, wherein the domains form an array and wherein the probe is sized to interrogate a single cell.

42. An apparatus for analyzing a sample comprising a probe, the probe comprising a pointed member, the pointed member having a plurality of domains disposed thereon, wherein the domains form an array and wherein the pointed member is sized to be inserted into a cell.

43. An apparatus for analyzing a sample comprising a probe, the probe comprising a pointed member, the pointed member having a plurality of domains disposed thereon, wherein the domains form an array and wherein at least one domain has a substance reversibly attached thereto reversibly attached by a tether, the tether comprising a protease substrate, a photolyzable tether, a chemically reactive tether, an ionically reactive tether, or a thermally sensitive tether.

* * * * *